United States Patent
Madabhushi et al.

(10) Patent No.: US 10,607,112 B2
(45) Date of Patent: Mar. 31, 2020

(54) PREDICTING BIOCHEMICAL RECURRENCE IN PRE-TREATMENT PROSTATE MAGNETIC RESONANCE IMAGING (MRI) WITH FIELD EFFECT INDUCED ORGAN DISTENSION (FORGE)

(71) Applicant: Case Western Reserve University, Cleveland, OH (US)

(72) Inventors: Anant Madabhushi, Shaker Heights, OH (US); Soumya Ghose, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 196 days.

(21) Appl. No.: 15/919,865

(22) Filed: Mar. 13, 2018

(65) Prior Publication Data

US 2018/0276497 A1    Sep. 27, 2018

Related U.S. Application Data

(60) Provisional application No. 62/474,255, filed on Mar. 21, 2017.

(51) Int. Cl.
*G06K 9/62* (2006.01)
*G06T 7/174* (2017.01)
(Continued)

(52) U.S. Cl.
CPC ............ *G06K 9/6227* (2013.01); *A61B 5/055* (2013.01); *A61B 5/4381* (2013.01);
(Continued)

(58) Field of Classification Search
None
See application file for complete search history.

(56) References Cited

U.S. PATENT DOCUMENTS

| | | | |
|---|---|---|---|
| 2013/0171639 A1* | 7/2013 | Sokolova | C12Q 1/6886 435/6.11 |
| 2014/0294279 A1* | 10/2014 | Madabhushi | G06T 7/0014 382/133 |

(Continued)

OTHER PUBLICATIONS

Shukla-Dave, Amita, et al. "Prediction of prostate cancer recurrence using magnetic resonance imaging and molecular profiles." Clinical Cancer Research 15.11 (2009): 3842-3849. (Year: 2009).*

(Continued)

*Primary Examiner* — Samah A Beg
(74) *Attorney, Agent, or Firm* — Eschweiler & Potashnik, LLC

(57) ABSTRACT

Embodiments predict prostate cancer (PCa) biochemical recurrence (BCR) employing an image acquisition circuit that accesses a pre-treatment image of a region of tissue demonstrating PCa; a segmentation circuit that segments a prostate capsule represented in the image; a registration circuit that registers the segmented prostate with a BCR-median template, and generates a registered surface of interest (SOI) mask by registering an SOI mask with the registered prostate; a mask circuit that generates a patient-specific SOI mask from the registered prostate and the registered SOI mask, and generates a patient-specific SOI mesh from the patient-specific SOI mask; a field effect induced organ distension (FOrge) circuit extracts a set of FOrge features from the patient-specific SOI mesh, and computes a probability that the region of tissue will experience BCR; and a classification circuit classifies the region of tissue as likely to experience BCR based on the probability.

27 Claims, 8 Drawing Sheets

(51) Int. Cl.
*G06T 7/33* (2017.01)
*A61B 5/055* (2006.01)
*A61B 5/00* (2006.01)
*G06K 9/68* (2006.01)
*G06T 7/11* (2017.01)
*G06T 7/00* (2017.01)
*G06K 9/32* (2006.01)

(52) U.S. Cl.
CPC .......... *A61B 5/4842* (2013.01); *G06K 9/3233* (2013.01); *G06K 9/6221* (2013.01); *G06K 9/685* (2013.01); *G06T 7/0014* (2013.01); *G06T 7/11* (2017.01); *G06T 7/174* (2017.01); *G06T 7/337* (2017.01); *A61B 5/7267* (2013.01); *A61B 2576/02* (2013.01); *G06K 2209/053* (2013.01); *G06T 2207/10088* (2013.01); *G06T 2207/20076* (2013.01); *G06T 2207/20081* (2013.01); *G06T 2207/30081* (2013.01); *G06T 2207/30096* (2013.01)

(56) References Cited

U.S. PATENT DOCUMENTS

| | | | |
|---|---|---|---|
| 2016/0196647 A1* | 7/2016 | Madabhushi | A61B 5/4381 |
| 2017/0053090 A1* | 2/2017 | Viswanath | A61B 34/10 |
| 2018/0276498 A1* | 9/2018 | Madabhushi | G06K 9/6227 |
| 2018/0336395 A1* | 11/2018 | Madabhushi | G06K 9/00147 |
| 2019/0251687 A1* | 8/2019 | Madabhushi | G06K 9/0014 |

OTHER PUBLICATIONS

Teverovskiy, Mikhail, et al. "Improved prediction of prostate cancer recurrence based on an automated tissue image analysis system." 2004 2nd IEEE International Symposium on Biomedical Imaging: Nano to Macro (IEEE Cat No. 04EX821). IEEE, 2004. (Year: 2004).*

* cited by examiner

PREDICTING BIOCHEMICAL RECURRENCE IN PRE-TREATMENT PROSTATE MAGNETIC RESONANCE IMAGING (MRI) WITH FIELD EFFECT INDUCED ORGAN DISTENSION (FORGE)

CROSS REFERENCE TO RELATED APPLICATIONS

This application claims the benefit of U.S. Provisional Application 62/474,255, filed Mar. 21, 2017.

FEDERAL FUNDING NOTICE

The invention was made with government support under National Institute of Health National Cancer Institute grant 1R01CA208236-01A1. The government has certain rights in the invention.

BACKGROUND

Magnetic resonance (MR) imaging (MRI) is routinely used to diagnose prostate cancer (PCa) and identify the stage of PCa. PCa may induce changes in the shape of the prostate capsule and central gland (CG) in biopsy positive (Bx+) patients relative to biopsy negative (Bx−) patients, elevated-prostate specific antigen (PSA) patients, or normal patients. PCa may also induce changes in the volume of the prostate and CG in Bx+ patients relative to Bx− patients, elevated-PSA patients, and normal patients. These changes in the shape and volume of the prostate may be observed in T2 weighted (T2w) MRI images.

Radiation therapy and radical prostatectomy are common treatments for PCa, with over 50% of PCa patients being treated with either or both treatments. However, radiation therapy has a failure rate as high as 25%, and 30-35% of treated PCa patients experience treatment failure within ten years. Predicting biochemical recurrence (BcR) prior to treatment may enable better planning and personalization of treatment. MR images may be used to assist the prediction of BcR in PCa patients. However, when obvious extra-capsular spread of the disease is not present, conventional approaches employing MRI are not useful for distinguishing patients who will experience BcR from those who will not.

Multi-parametric MRI (mpMRI) is widely used in the management of PCa to improve the detection, tumor staging, and risk stratification for selection of patients for active surveillance and recurrence prediction of the disease. Despite its broad adoption in the management of PCa, conventional approaches using MRI, including mpMRI are susceptible to variability in MRI acquisition parameters, scanner protocols, image artifacts, and non-standardized image intensities. This variability may occur both within an individual institution (e.g., hospital, university) and across multiple institutions. Conventional approaches to MRI-based PCa diagnosis, identification, or prognosis prediction may employ protocols or guidelines for imaging acquisition parameters and findings reporting, although score interpretation and detection thresholds, particularly across multiple institutions, have not been uniformly applied or exhaustively studied. Furthermore, implementing protocols and guidelines across different institutions takes time, costs money, and puts a patient at additional risk if the guidelines and protocols are not consistently applied.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
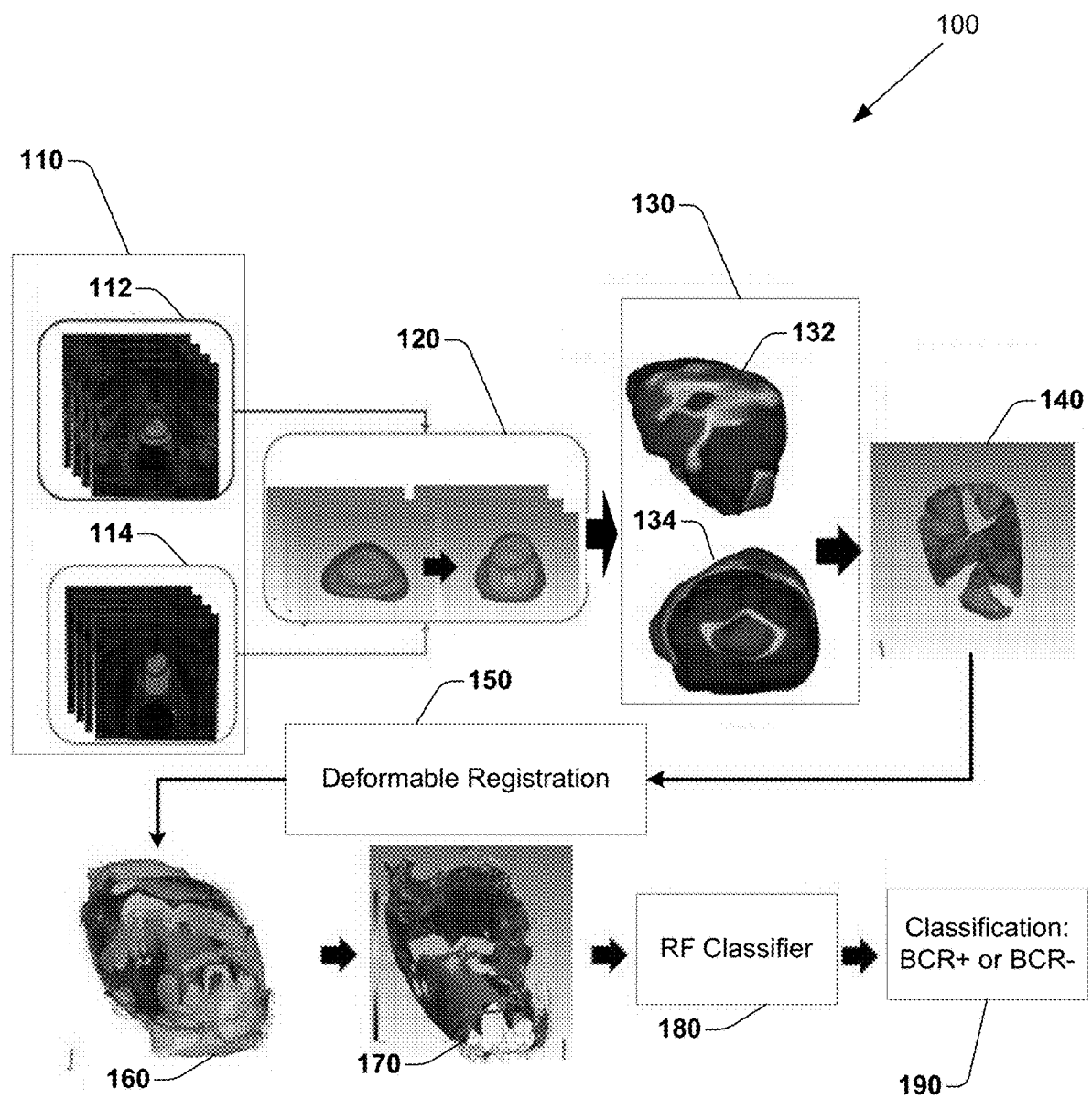
FIG. 1 is a schematic overview of an exemplary workflow for biochemical recurrence prediction.

Of the 180,890 new cases of prostate cancer diagnosed in USA in 2016 over 50% of these patients will be treated with either radical prostatectomy or radiation therapy or both. Despite advancement in treatment there is treatment failure in an estimated 30-35% of the treated prostate cancer patients within 10 years of treatment. An elevated prostate specific antigen (PSA), for example, 0.2 ng/ml for surgery or 2 ng/ml for radiation therapy above the nadir, is indicative of treatment failure or biochemical recurrence (BCR). BCR is often associated with the presence of more aggressive metastatic prostate cancer and hence worse prognosis. Embodiments described herein detect or predict with greater accuracy BCR in patients with prostate cancer undergoing definitive therapy and facilitate identifying patients who would benefit from adjuvant or neo-adjuvant therapies, or other types of therapy.

Multi-parametric magnetic resonance imaging (mpMRI) is used for PCa detection, tumor staging, risk stratification for selection of men for active surveillance, and recurrence prediction. Radiomics or computer extracted texture features provide alternative feature representations and may be used for risk characterization and disease diagnosis. Radiomic features extracted from prostate tissue images in T2w MRI may be predictive of BCR. However, radiomic features extracted from mpMRI are susceptible to scanner variations, variations in acquisition protocols, image artifacts, and non-standardized image intensities.

Aggressive prostate cancer may induce organ distensions. For example, a tumor that is expanding and growing might be inducing stresses on the surrounding tissue which in turn might ripple over to the surface of the capsule. Thus a tumor field effect may manifest in the form of distensions to the capsule surface, and more and less aggressive tumors might differentially distend the capsule surface. On a T2w MRI scan, this distension may present as an irregular bulge and focal capsular retraction. Differences may manifest in the surface of the prostate capsule between prostates with or without cancer.

Field effect that is strongly correlated to recurrence and that may mechanically deform prostate capsule surface far beyond the tumor periphery is however not interrogated in conventional recurrence prediction approaches. BCR is often associated with aggressive cancer growth, one that might induce a field effect deformation. Embodiments described herein quantify differential localized deformation of the prostate SOI that arise from the field effect of aggressive growth of the confined tumor for BCR+ patients. Embodiments quantify such localized deformation with deformation magnitude and orientation features to discriminate BCR+ and BCR− patients.

Embodiments extract prostate capsule distension features from pre-treatment MRI images that quantify prostate capsule deformation magnitude and orientation, and predict BCR based on the extracted features. Embodiments identify spatially contextual SOI of the capsule from which the distension features are extracted. Embodiments may train a machine learning classifier with pre-treatment MRI images acquired from a first institution or that were acquired with a first set of imaging parameters, and test the machine learning classifier with a validation or testing set acquired from a different institution or with a second, different set of imaging parameters. The prostate distension features are based on prostate capsule deformation estimated from segmentation of the prostate and are more resilient to scanner and acquisition parameter variability than conventional approaches.

Embodiments predict BCR by creating BCR+ and BCR− cohort atlases, identifying the SOI that significantly differs between the BCR+ and BCR− atlases, and extracting field effect induced organ distension (FOrge) features from the SOI. The FOrge features are provided to a machine learning classifier, which computes a probability to predict BCR.

In one embodiment, a BCR+ atlas and a BCR− atlas are constructed. An atlas is a representative model of specific characteristics of a given population. A visual anatomic atlas of an organ (e.g., prostate) for a specific class (e.g., BCR+, BCR−) may be generated by registering individual three dimensional (3D) volume meshes to a representative template. A set of pre-treatment images of a region of tissue demonstrating PCa is accessed. Spatially contextual SOI of the prostate capsule are uniquely identified from statistically significant shape differences between BCR+ and BCR− atlases created from the training images. To create subpopulation atlases of each of the groups, prostates inside a given subpopulation (i.e. BCR+ or BCR−) are registered to a representative template. The prostate with median volume for each of the group is selected as the representative template. A segmented mask of the prostate is used to provide anatomical constraint and improve registration accuracy. Registration of the prostate to the representative template is performed in two stages: in a first stage, an initial affine registration is performed followed in a second stage by a non-rigid registration. A block matching strategy is employed to determine the transformation parameters for the affine registration. The affine registration of the moving image to the reference image is followed with a B-spline-based non-rigid registration. The segmented masks of the prostate capsules were given the same transformation as the registered images.

In one embodiment, members of the set of pre-treatment images are first registered (i.e., aligned) to a common canonical frame for statistical comparison. In this example, members of the set of pre-treatment images are T2w prostate MRI images, and alignment of members of the set of pre-treatment images is performed in two stages. In the first stage all, or a threshold number of, prostate MRI images for a given subpopulation (e.g., BCR+ or BCR−) are aligned to the representative template of that group to create a representative atlas of each of the BCR+ and BCR− groups. In the second stage the BCR+ and BCR− atlases are registered to a common space for statistical analysis and comparisons.

Embodiments define a spatially contextual surface of interest from which to compare BCR+ and BCR− prostates. To perform a statistical comparison of the prostate capsule shape between BCR+ and BCR− patients, a BCR+ atlas created for BCR+ patients is registered to a BCR− atlas of the BCR− patients. All, or a threshold number of, the registered prostate capsules, of both the BCR+ and BCR− groups are isotropically scaled with 0.3 mm$^3$ resolution and transformed into a signed distance function. As opposed to the binary representation of a mask where each voxel within the prostate capsule has a value of 1 and a value of 0 outside the capsule, the value assigned to each voxel is determined based on the distance of a given voxel from the capsule boundary. Consequently, the signed distance function yields positive values for voxels inside the prostate capsule, while the value of the voxel decreases as it approaches the boundary where the signed distance function is zero, becomes negative outside the prostate capsule, and continues to decrease depending on the distance of the voxel from the prostate capsule.

The signed distance representation gives an implicit representation of the prostate boundary and aids in a t-test based comparison of the shape in a non-parametric General Linear Model (GLM) based t-test framework. Statistically significant shape differences are quantified using 5000 random permutation testing in which the p-value is corrected for multiple comparison. A voxel is considered as belonging to a region exhibiting statistically significant differences between shapes for BCR+ and BCR− patients if the p-value estimated by this testing is less than 0.05. Significant shape differences between BCR+ and BCR− cohorts are then quantified as an SOI. FIG. 1 illustrates an example framework for quantifying statistical shape differences.

FIG. 1 is a schematic overview of an example workflow 100 for quantifying statistical shape differences. FIG. 1 illustrates, at 110, a set of registered BCR+ prostate capsule masks 112, and a set of registered BCR− prostate capsule masks 114. At 120, a generalized linear model based T-test is applied to the set of registered BCR+ prostate capsule masks 112 and the set of registered BCR− prostate capsule masks 114 to identify shape differences. At 130, statistically significant differences in the shape of prostate capsules are computed. A sagittal view 132 and an axial view 134 of a prostate capsule are illustrated. At 140, an SOI that is significantly different between the BCR+ and the BCR− cohorts is identified. At 150, the SOI is deformably registered to a prostate capsule that is being analyzed. An image of the SOI deformably registered and overlaid on the prostate capsule is illustrated at 160. A set of curvature and surface normal features are extracted from the SOI at 170. The set of curvature and surface normal features are provided to a machine learning classifier, in this example a random forest classifier, at 180. The random forest classifier computes a probability that the prostate capsule will experience BCR, and at 190, a classification of the prostate capsule as likely to experience BCR or unlikely to experience BCR is produced.

Embodiments quantify the irregular deformation of the prostate capsule by extracting, from the SOI, curvature magnitude and surface normal orientation features. The surface curvature and orientation features are however more meaningful in the spatially contextual SOI which is significantly different between the BCR+ and BCR− cohorts, than in similar features extracted over the entire surface of the prostate capsule. To extract the curvature and surface orientation features from spatially contextual SOI, patient images are rigidly registered to the BCR− template selected for statistical comparison of BCR+ and BCR− cohorts. The SOI mask identified via population based statistical comparison is then registered to patient mask using a B-spline based registration. This ensures that a patient mask is not deformed and remains unaffected. The registered mask is then considered as an SOI for conversion to an SOI mesh, and for feature extraction.

The SOI mask for the new patient is then converted to a SOI mesh. An SOI mesh includes a plurality of vertices. The surface normal orientation provides the direction of the surface deformation and surface Gaussian and mean curvature provides the magnitude of the deformation. Curvature and normal orientation features are extracted for vertices of the mesh.

In one embodiment, the surface normal orientation provides the direction of the surface deformation and surface Gaussian curvature provides the magnitude. Gaussian curvature and normal orientation features are extracted for vertices of the mesh. Kth Gaussian curvature discretized at vertex v is given by:

$$K_v = 2 \times PI - \sum_{\nabla} (v_\gamma)$$

where $\Sigma_\nabla$ is the summation of all facets and $v_\gamma$ is the orientation at $\gamma$. For a vertex the normal orientation is represented in a spherical coordinate system and $\theta$ (the angle between the projection of the normal vector in XY plane and X axis) and $\phi$ (the angle between the projection of the normal vector in Y Z plane and Z axis) are extracted.

In one embodiment, for every patient three arrays of curvature, and $\theta$ and $\phi$ are created and statistical measures including mean, standard deviation, inter-quartile range (Q1 and Q3), range, skewness and kurtosis are extracted. Thus the dimension of the feature vector for a patient is 21, derived from three features (curvature, $\theta$ and $\phi$) and seven statistical measures (mean, standard deviation, inter-quartile range (Q1 and Q3), range, skewness and kurtosis) for each of the three features.

In another embodiment, for every patient four arrays, Gaussian curvature, mean curvature, $\theta$ and $\phi$ (3d orientation in spherical coordinate system) are created and statistical measures like mean, standard deviation, inter-quartile range (Q1 and Q3), range, skewness and kurtosis are extracted. Thus the dimension of the feature vector for a patient was 28, derived from four features (Gaussian curvature, mean curvature, $\theta$ and $\phi$) and seven statistical measures (mean, standard deviation, inter-quartile range (Q1 and Q3), range, skewness and kurtosis) for each of the four features. A non-parametric Gini importance based feature selection technique is used to select the most discriminative features. Gaussian curvature and normal orientation do not follow a normal distribution. Thus, conventional feature selection strategies are not effective in selecting discriminative features that are based on Gaussian curvature and normal orientation. In another embodiment, other techniques for selecting discriminative features may be employed.

Figure 2:
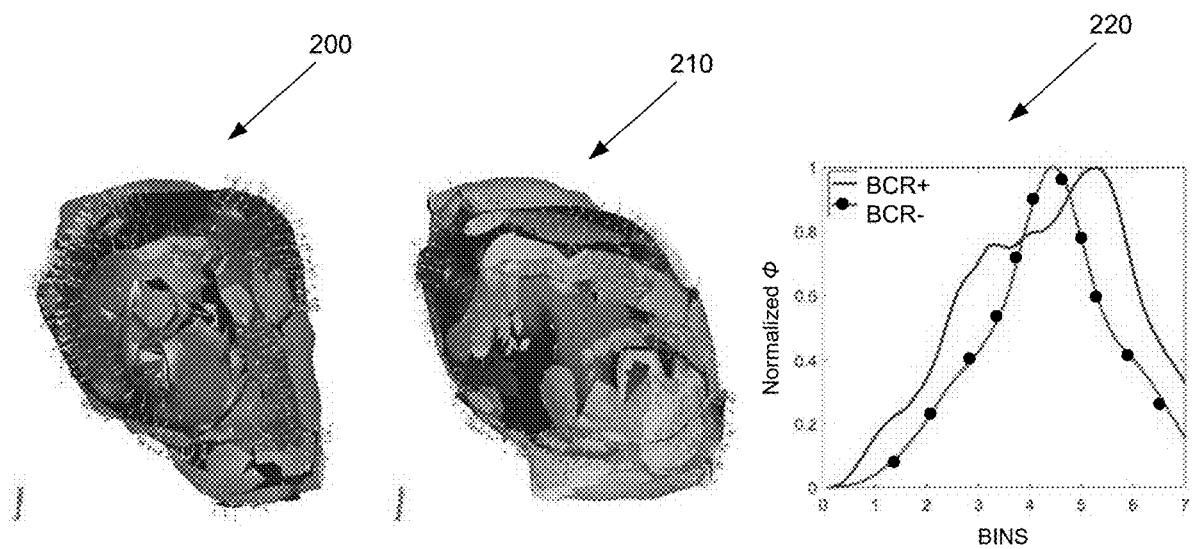
FIG. 2 illustrates a surface of interest (SOI) overlaid on a prostate capsule.

FIG. 2 illustrates, at 200, an SOI mask overlaid on a BCR+ prostate capsule. FIG. 2 also illustrates, at 210, the SOI mask overlaid on a BCR− prostate capsule. FIG. 2 further illustrates a graph 220 of the differential distribution of $\phi$ (the angle between the projection of the normal vector in Y Z plane and Z axis) between the BCR+ SOI and the BCR− SOI. The x-axis of graph 220 indicates the number of bins, and the y-axis indicates the normalized $\phi$.

Example methods and apparatus demonstrably improve on conventional technologies for predicting BCR. For example, embodiments described herein predict BCR with an average area under the curve (AUC) of at least 0.72 and an accuracy of at least 0.78+−0.21, compared with conventional predictive techniques that employ other types of features. For instance, conventional approaches that employ clinical variables such as PSA, Gleason, and PIRADS-v2 to construct a linear discriminant analysis (LDA) classifier trained on the same training set as embodiments described herein, achieve an AUC of only 0.57.

By increasing the accuracy with which BCR is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader and intra-reader variability among human radiologists or oncologists. Example methods and apparatus thus improve on conventional methods in a measurable, clinically significant way. When implemented as part of a personalized medicine system, a computer assisted diagnostic (CADx) system, or a BCR prediction system which may include a computer or a processor configured to predict BCR, example embodiments improve the performance of a machine, computer, or computer-related technology by providing a more accurate and more reliable prediction of disease recurrence compared to conventional approaches to controlling a machine to predict disease recurrence.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 3:
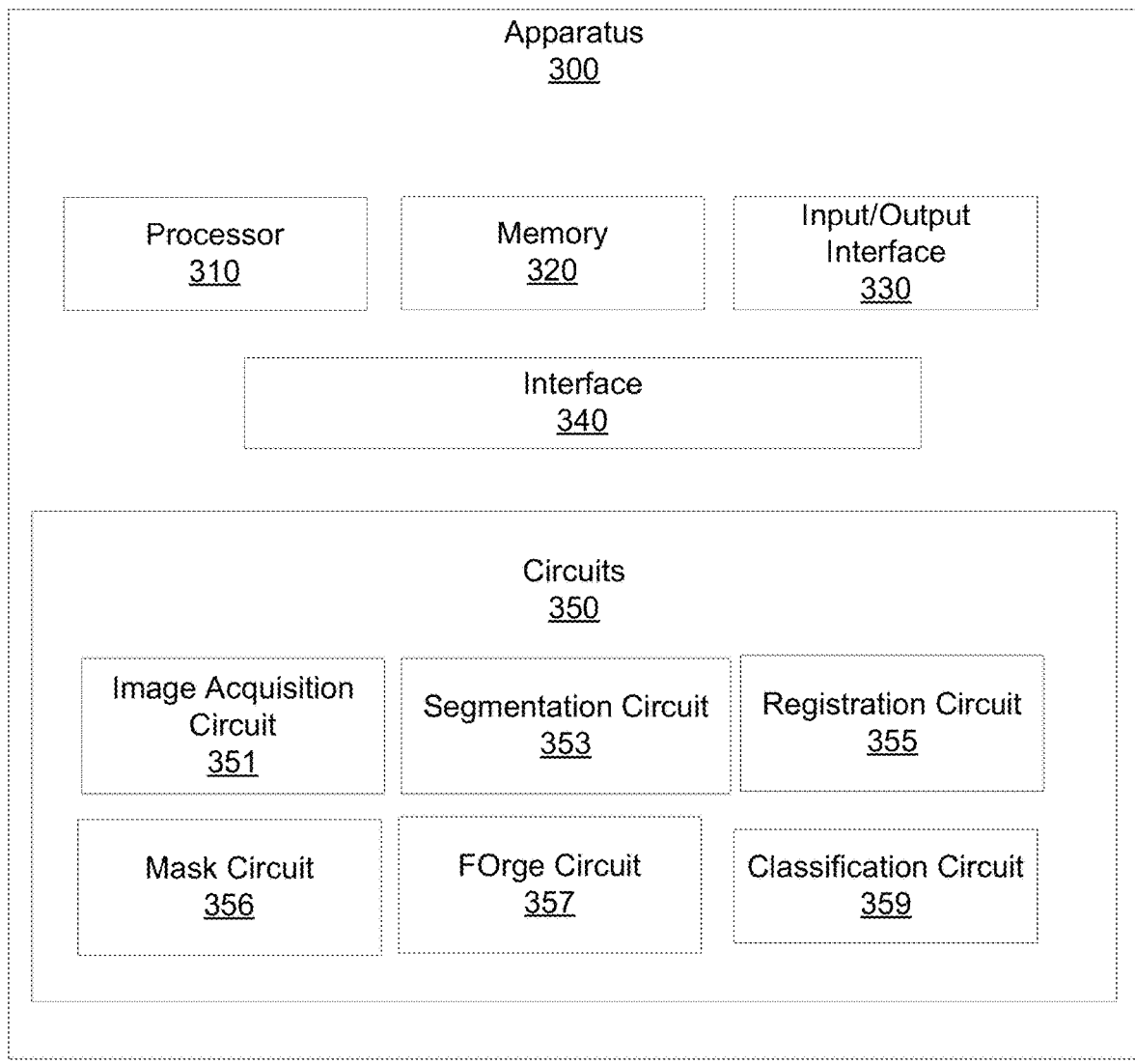
FIG. 3 illustrates an example apparatus for predicting BcR.

FIG. 3 illustrates an example apparatus 300 that predicts prostate cancer BCR. Apparatus 300 includes a processor 310. Apparatus 300 also includes a memory 320. Processor 310 may, in one embodiment, include circuitry such as, but not limited to, one or more single-core or multi-core processors. Processor 310 may include any combination of general-purpose processors and dedicated processors (e.g., graphics processors, application processors, etc.). The processors may be coupled with or may include memory (e.g. memory 320) or storage and may be configured to execute instructions stored in the memory or storage to enable various apparatus, applications, or operating systems to perform the operations. Memory 320 is configured to store a digitized image of a region of tissue demonstrating cancerous pathology. In one embodiment, memory 320 is configured to store an image of a region of tissue demonstrating PCa, a BCR negative (BCR−) median template, and a surface of interest (SOI) mask. Apparatus 300 also includes an input/output (I/O) interface 330. Apparatus 300 also includes a set of circuits 350. The set of circuits 350 includes an image acquisition circuit 351, a segmentation circuit 353, a registration circuit 355, a mask circuit 356, a field effect induced organ distension (FOrge) circuit 357, and a classification circuit 359. Apparatus 300 further includes an interface 340 that connects the processor 310, the memory 320, the I/O interface 330, and the set of circuits 350.

Image acquisition circuit 351 is configured to access an image of a region of tissue demonstrating cancerous pathology. The image may be a pre-treatment image of a region of tissue demonstrating PCa. The image includes a plurality of pixels, a pixel having an intensity. Accessing the image includes acquiring electronic data, reading from a computer file, receiving a computer file, reading from a computer memory, or other computerized activity. In another embodiment, accessing the image may include accessing a network attached storage (NAS), a cloud storage system, or other type of electronic storage system. Accessing the image may, in one embodiment, include accessing a NAS device, a cloud storage system, or other type of electronic storage system using input/output interface 330. In one embodiment, the image is a T1 W MRI image, or a T2 W MRI image. In another embodiment, other imaging modalities, approaches, or parameters may be used to generate and access the image accessed by image acquisition circuit 351.

In one embodiment, image acquisition circuit 351 is configured to pre-process the image. Pre-processing the image may include applying N4 bias field correction to the image to reduce magnetic bias. In another embodiment, other pre-processing techniques may be employed.

Segmentation circuit 353 is configured to generate a segmented prostate by segmenting a prostate capsule represented in the pre-treatment image. In one embodiment, segmentation circuit 353 is configured to segment the prostate capsule using a statistical shape and appearance model-based segmentation technique.

Registration circuit 355 is configured to generate a registered prostate by registering the segmented prostate with the BCR− median template. The BCR− median template is the image of the prostate with median volume for the BCR− group used to generate the BCR− atlas. Registration circuit 355 is further configured to generate a registered SOI mask by registering the SOI mask with the registered prostate. In one embodiment, registration circuit 355 is configured to register the segmented prostate with the BCR− median template using a rigid registration technique. In one embodiment, registration circuit is 355 configured to register the SOI mask with the registered prostate using a B-spline registration technique. In one embodiment, registration circuit 355 is configured to employ an affine registration technique. In this embodiment, a block matching strategy is employed to determine the transformation parameters for the affine registration.

Mask circuit 356 is configured to generate a patient-specific SOI mask from the registered prostate and the registered SOI mask. The patient-specific SOI mask defines a surface area of the prostate capsule represented in the pre-treatment image that corresponds with the SOI mask identified as having statistically significant shape differences between members of a BCR+ atlas and a BCR− atlas. Mask circuit 356 is further configured to generate a patient-specific SOI mesh from the patient-specific SOI mask. The patient-specific SOI mesh includes a plurality of vertices from which FOrge features may be extracted.

FOrge circuit 357 is configured to extract a set of FOrge features from the patient-specific SOI mesh. FOrge circuit 357 is further configured to compute a probability that the region of tissue will experience BCR based, at least in part, on the set of FOrge features. In one embodiment, the set of FOrge features includes a curvature magnitude feature, an XY plane surface normal orientation feature, and an XZ plane surface normal orientation feature. In this embodiment, the set of FOrge features further includes a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature. In another embodiment, the set of FOrge features may include other, different features.

In one embodiment, FOrge circuit 357 includes a machine learning component. The machine learning component is configured to compute the probability based on the set of FOrge features. In one embodiment, the machine learning component is configured as a random forest (RF) classifier having a depth of two, and 10000 trees. In another embodiment, the machine learning component may be configured as an RF classifier with other, different parameters. In another embodiment, the machine learning component may be another different type of machine learning classifier, including a support vector machine (SVM), a linear discriminant analysis (LDA) classifier, a quadratic discriminant analysis (QDA) classifier, a convolutional neural network (CNN), or other type of machine learning or deep learning classifier.

Classification circuit 359 is configured to classify the region of tissue as likely to experience BCR or unlikely to experience BCR based, at least in part, on the probability. In one embodiment, classification circuit 359 computes the probability based, at least in part, on the probability and at least one of: the set of FOrge features, the patient-specific SOI mask, the patient-specific SOI mesh, or the image. In one embodiment, classification circuit 359 is configured as a machine learning classifier. For example, classification circuit 359 may be configured as a linear discriminant analysis (LDA) classifier, a quadratic discriminant analysis (QDA) classifier, a support vector machine (SVM) classifier, or a random forest (RF) classifier.

Embodiments described herein, including apparatus 300, resolve features extracted from the image at a higher order or higher level than a human can resolve in the human mind or with pencil and paper. For example, the curvature magnitude feature, the XY plane surface normal orientation feature, and the XZ plane surface normal orientation feature are not biological properties of cancerous tissue that a human eye can perceive. A human prostate does not come with an overlaid SOI mesh, and an SOI mesh cannot be stored in a human mind. The set of FOrge features provided to the machine learning classifier is of a different nature than the prostate capsule represented in the image, or the patient-specific SOI mask. The probability computed by FOrge circuit 357 and the classification generated by classification circuit 359 are of a fundamentally different nature than the image or the radio frequency signal acquired from the region of tissue to generate the MRI image.

Figure 4:
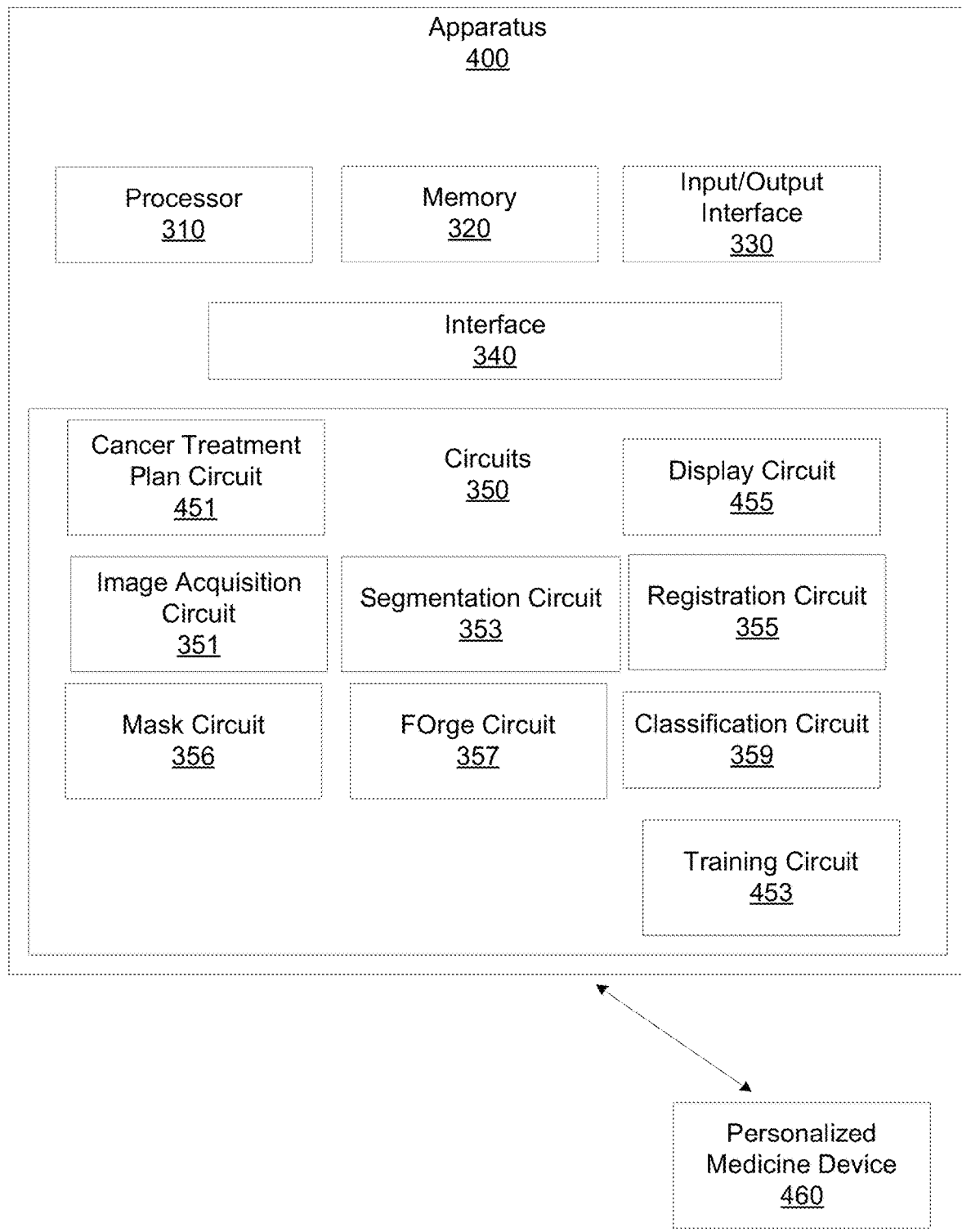
FIG. 4 illustrates an example apparatus for predicting BcR.

FIG. 4 illustrates an example apparatus 400 that is similar to apparatus 300 but that includes additional details and elements. In one embodiment of apparatus 400, the set of circuits 350 further includes a cancer treatment plan circuit 451. Cancer treatment plan circuit 451 is configured to generate a cancer treatment plan for the patient of which the image was acquired based, at least in part, on the classification, and at least one of the probability, the set of FOrge features, the patient-specific SOI mask, or the image. Defining a personalized cancer treatment plan facilitates delivering a particular treatment that will be therapeutically active to the patient, while minimizing negative or adverse effects experienced by the patient. For example, the cancer treatment plan may suggest a surgical treatment, may define an immunotherapy agent dosage or schedule, or a chemotherapy agent dosage or schedule, for a patient identified as likely to experience BCR. For a patient classified as unlikely to experience BCR, other treatments may be suggested.

In another embodiment, apparatus 400 may control a computer aided diagnosis (CADx) system to classify the region of tissue represented in the image based, at least in part, on the probability or the classification generated by classification circuit 359. In other embodiments, other types of CADx systems may be controlled, including CADx systems for predicting recurrence or progression in other tissue presenting other, different pathologies that may be distinguished based on FOrge features. For example, embodiments described herein may be employed to predict disease progression or recurrence based on probabilities computed from FOrge features by a machine learning classifier in breast cancer (BCa), kidney disease, lung cancer, or brain pathologies.

In another embodiment of apparatus 400, the set of circuits 350 further includes a training circuit 453 configured to train classification circuit 357. Training classification circuit 357 may include training a machine learning classifier. In one embodiment, training circuit 453 is configured to access a dataset of digitized images of a region of tissue demonstrating PCa. The dataset of digitized images includes, in this example, pre-treatment T1 W MRI images, or pre-treatment T2 W MRI images. In one embodiment, training circuit 453 is configured to control image acquisition circuit 351 to access the dataset of digitized images of a region of tissue demonstrating PCa.

In one embodiment, training the machine learning classifier includes generating a BCR+ atlas, and a BCR− atlas. In this embodiment, training circuit 453 is configured to generate the BCR+ atlas and the BCR-atlas by accessing a set of pre-treatment images of a region of tissue demonstrating PCa. Accessing the set of pre-treatment images includes acquiring electronic data, reading from a computer file, receiving a computer file, reading from a computer memory, or other computerized activity. The set of pre-treatment images includes a plurality of BCR+ images and a plurality of BCR− images. Training circuit 453 is also configured to generate a pre-processed set by pre-processing the set of pre-treatment images using N4 bias field correction to reduce magnetic bias.

Training circuit 453 is also configured to select a BCR+ subset from the pre-processed set. Training circuit 453 is also configured to select a BCR− subset from the pre-processed set. In one example embodiment, generating a BCR+ atlas and a BCR− atlas may include selecting MRI images of prostates from a prostate MRI registry of at least 874 patients. Availability of complete image datasets including T1w, T2w and apparent diffusion coefficient (ADC) maps, absence of treatment for PCa before MRI, presence of clinically localized PCa, Gleason scores available from pretreatment biopsy and/or from radical prostatectomy specimens, and post-treatment outcome data including post-treatment PSA and a minimum of 3 years of follow-up may be used as inclusion criteria for selection into the BCR+ subset or the BCR− subset. In this example, of the 874 patients in the registry, 80 cases met these inclusion criteria. BCR+ and BCR− cases for atlas creation are selected from these 80 patients. To reduce statistical biases of the atlases, equal number of patients in BCR+ and BCR− cohorts (25 each); similar Gleason scores (6 to 9); and similar tumor stages (T2 to T3) are used to identify, in this example, 50 patients. The remaining 30 patients out of 80 are used for validation. The BCR+ patients had a mean recurrence time of 18.5 months. The BCR− patients had a mean follow-up time of 4.2 years. In another embodiment, other parameters may be employed to select subsets and generate the atlases.

Training circuit 453 is also configured to segment a prostate capsule represented in a member of the BCR+ subset. Training circuit 453 is also configured to segment a prostate capsule represented in a member of the BCR− subset. In one embodiment, training circuit 453 is configured to automatically segment a the prostate capsule represented in a member of the BCR+ subset or the BCR− subset using a statistical shape and appearance model. In one embodiment, a shape and appearance model of a prostate is created from a manual segmentation of the prostate. A training set of segmented prostates may be generated. Given an un-segmented prostate, the statistical shape and appearance model automatically segments the prostate by minimizing appearance/intensity differences between the created model and the un-segmented prostate constrained by the statistical shape of the prostate learnt from a training set. In one embodiment, training circuit 453 is configured to control segmentation circuit 353 to segment a prostate capsule represented in a member of the BCR+ subset and to segment a prostate capsule represented in a member of the BCR− subset.

Training circuit 453 is also configured to select a BCR+ median image from the BCR+ subset. Training circuit 453 is also configured to select a BCR− median image from the BCR− subset. Selecting the BCR+ median image or the BCR− median image includes selecting the image of the prostate with median volume for the BCR+ subset or the BCR− subset.

Training circuit 453 is also configured to generate a BCR+ atlas by registering a member of the BCR+ subset to the BCR+ median image. Training circuit 453 is further configured to generate a BCR− atlas by registering a member of the BCR− subset to the BCR− median image.

The BCR+ atlas and the BCR− atlas are employed by embodiments described herein to perform a statistical comparison of the prostate capsule shape between BCR+ and BCR− patients. To perform a statistical comparison of the prostate capsule shape between BCR+ and BCR− patients, embodiments described herein register the BCR+ atlas images to the BCR− atlas images. In one embodiment, a threshold number (e.g., 100%, 90%, 75%) of registered prostate capsules of both the BCR+ and BCR− groups are isotropically scaled with 0.3 mm$^3$ resolution and transformed into a signed distance function. Isotropic scaling facilitates obtaining images with identical inter-voxel spacing in three dimensions. As opposed to the binary representation of a mask where each voxel within the prostate capsule has a value of 1 and a value of 0 outside the capsule, the value assigned to each voxel is determined by embodiments described herein based on the distance of a given voxel from the capsule boundary. Consequently, the signed distance function yields positive values for voxels inside the prostate capsule, while the value of the voxel decreases as it approaches the boundary where the signed distance function is zero, becomes negative outside the prostate capsule, and continues to decrease depending on the distance of the voxel from the prostate capsule.

The signed distance representation gives an implicit representation of the prostate boundary and aids in a t-test based comparison of the shape in a non-parametric General Linear Model (GLM) based t-test framework. Statistically significant shape differences are quantified with random permutation testing with the p-value being corrected for multiple comparisons. A voxel is considered as belonging to a region exhibiting statistically significant differences between shapes for BCR+ and BCR− patients if the p-value estimated by this testing is less than 0.05. Voxels of the prostate surface demonstrating significant shape differences between BCR+ and BCR− cohorts are then quantified as the SOI.

The population based statistics used to identify spatially contextual SOI that significantly differs between the two cohorts is, however, dependent on the quality of the registration of the atlases. Thus, embodiments may consider registration accuracy presented in terms of Dice similarity coefficient (DSC) and mean absolute surface distance (MASD). In one embodiment, the DSC of the BCR+ atlas is at least 0.98+−0.01 and that of the BCR− atlas is at least 0.97+−0.01. In this example, the MASD of the BCR+ atlas is at least 0.30+−0.11 mm and that of the BCR− atlas is at least 0.40+−0.14 mm. Embodiments facilitate ensuring atlas registration accuracy sufficient for statistical shape comparison that results in BCR prediction accuracy that is greater than conventional approaches. In another embodiment, other parameters may be employed to ensure the registration accuracy of the atlases.

FIG. 4 also illustrates a personalized medicine device 460. Personalized medicine device 460 may be, for example, a CADx system, a prostate cancer BCR prediction system, or other type of personalized medicine device that may be used to facilitate the prediction of cancer progression or recurrence. In one embodiment, the cancer treatment plan circuit 451 may control personalized medicine device 460 to display the classification, the probability, the set of FOrge features, the cancer treatment plan, or the image on a computer monitor, a smartphone display, a tablet display, or other displays. In one embodiment, cancer treatment plan circuit 451 may control personalized medicine device 460 via I/O interface 330.

In one embodiment of apparatus 400, the set of circuits 350 further includes a display circuit 455. The display circuit 455 may control the cancer treatment plan circuit 451 or a CADx system to display the classification, the probability, the set of FOrge features, the cancer treatment plan, the patient-specific SOI mask, or the image on a computer monitor, a smartphone display, a tablet display, or other displays. Displaying the classification, the probability, the set of FOrge features, the cancer treatment plan, the patient-specific SOI mask, or the image may also include printing the classification, the probability, the set of FOrge features, the cancer treatment plan, the patient-specific SOI mask, or the image. Display circuit 455 may also control the CADx system to display operating parameters or characteristics of the classification circuit 359, including a machine learning classifier, during both training and testing, and during clinical operation. Displaying the classification, the probability, the set of FOrge features, the cancer treatment plan, or the image involves but is not limited to extracting and changing the character of information present in a region of tissue (e.g. biological tissue), to a radiological image (e.g. MRI image), to changing the information present in the image to information of a different character in the set of FOrge features, the probability, the characterization, and the cancer treatment plan. Embodiments described herein further transform the character of information to information suitable for display on, for example, a computer monitor, a smartphone display, a tablet display, or other displays. Thus, embodiments described herein use a combined order of specific rules, elements, or components that render information into a specific format that is then used and applied to create desired results more accurately and with greater reliability than conventional approaches.

Figure 5:
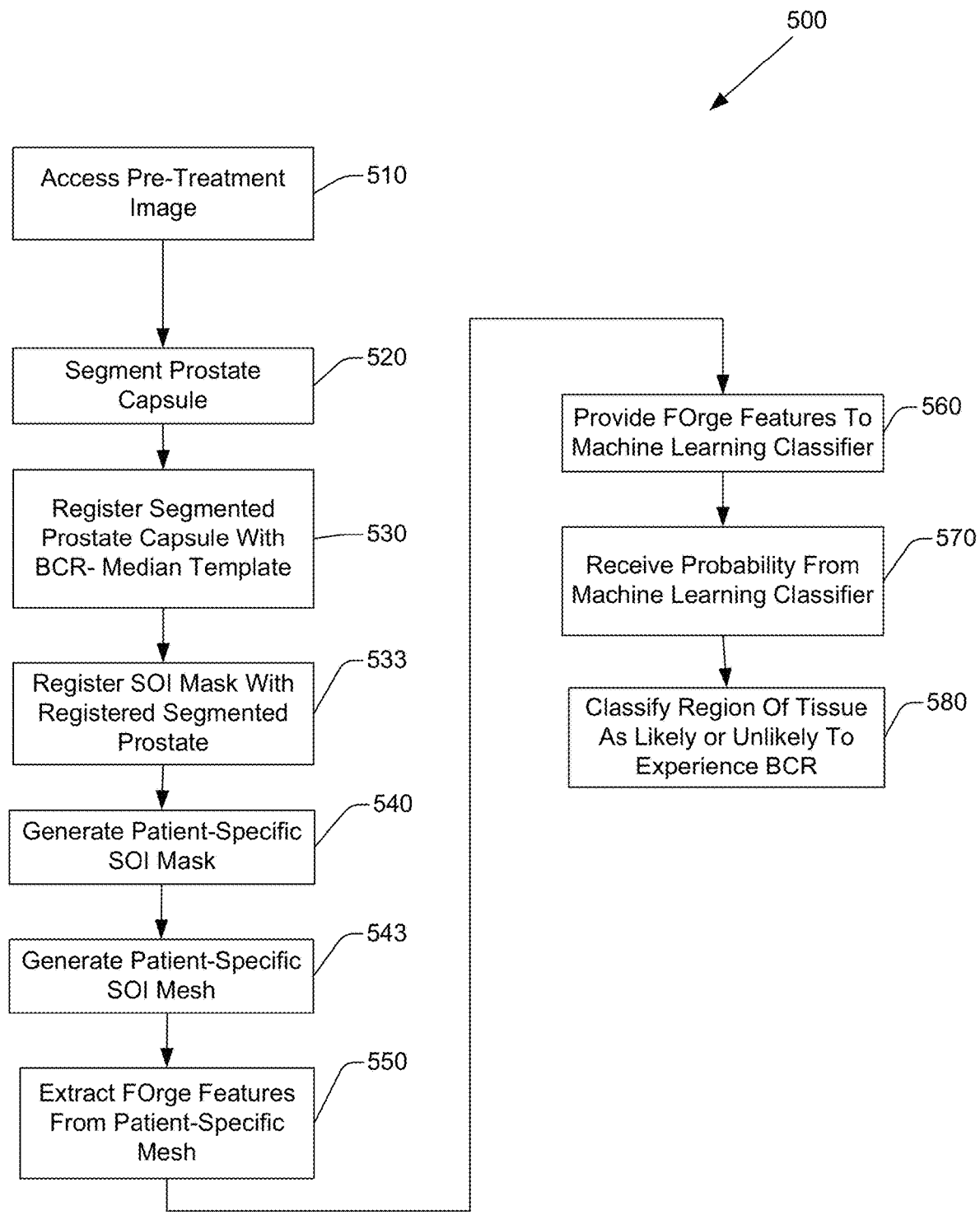
FIG. 5 illustrates an example method for predicting BcR.

FIG. 5 illustrates a computerized method 500 for predicting biochemical recurrence. Method 500 includes, at 510, accessing a pre-treatment image of a region of tissue demonstrating cancerous pathology. In one embodiment, the image is a T1 W or T2 W MRI image of a region of tissue demonstrating PCa. The image includes a plurality of voxels, a voxel having an intensity. Accessing the image includes acquiring electronic data, reading from a computer file, receiving a computer file, reading from a computer memory, or other computerized activity. In other embodiments, the image may be of other, different types of tissue demonstrating other, different pathologies imaged using different imaging techniques or parameters. For example, in one embodiment, the image an MRI image of a different region of tissue demonstrating cancerous pathology in which field effect induced organ distension is predictive of biochemical recurrence. In another embodiment, the image is a computerized tomography (CT) image of region of tissue demonstrating cancerous pathology.

Method 500 also includes, at 520 segmenting a prostate capsule represented in the image. In one embodiment, method 500 may segment the prostate capsule represented in the image using a statistical shape and appearance based segmentation approach.

Method 500 also includes, at 530, registering the segmented prostate with a BCR− median template. In one embodiment, registering the segmented prostate with the BCR− median template includes registering the segmented prostate with the BCR− median template using a rigid registration technique. The BCR− median template is the image of the prostate with the median volume of the BCR− subset used for generating the BCR− atlas.

Method 500 also includes, at 533 registering a surface of interest (SOI) mask with the registered segmented prostate. In one embodiment, registering the SOI mask with the registered segmented prostate includes registering the SOI mask with the registered segmented prostate using a B-spline registration technique.

Method 500 also includes, at 540, generating a patient-specific SOI mask from the registered SOI. The patient-specific SOI mask defines a surface area of the prostate capsule represented in the pre-treatment image that corresponds with the SOI identified as having statistically significant shape differences between members of a BCR+ atlas and a BCR− atlas.

Method 500 also includes, at 543, generating a patient-specific SOI mesh from the patient-specific SOI mask. The SOI mesh includes a plurality of vertices.

Method 500 also includes, at 550, extracting a set of field effect induced organ distension (FOrge) features from the patient-specific SOI mesh. In one embodiment, the set of FOrge features includes a curvature magnitude feature, an XY plane surface normal orientation feature, and an XZ plane surface normal orientation feature. In this embodiment, the set of FOrge features further includes a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature.

Method 500 also includes, at 560, providing the set of FOrge features to a machine learning classifier. Providing the set of FOrge features to the machine learning classifier may include acquiring electronic data, reading from a computer file, receiving a computer file, reading from a computer memory, or other computerized activity. In one embodiment, the machine learning classifier is a random forest (RF) classifier having a depth of two, and 10000 trees. In another embodiment, the machine learning classifier is an LDA classifier, a QDA classifier, or an SVM classifier. In another embodiment, the machine learning classifier may be another, different type of machine learning classifier. In one embodiment, method 500 further includes training the machine learning classifier. In another embodiment, method 500 further includes testing the machine learning classifier on a held-out testing dataset.

Method 500 also includes, at 570, receiving, from the machine learning classifier, a probability that the region of tissue will experience BCR. The machine learning classifier computes the probability based, at least in part, on the set of FOrge features. Receiving the probability from the machine learning classifier may include acquiring electronic data, reading from a computer file, receiving a computer file, reading from a computer memory, or other computerized activity. In another embodiment, the machine learning classifier computes a second probability that the region of tissue will experience cancer progression based, at least in part, on the set of FOrge features.

Method 500 further includes, at 580, classifying the region of tissue as likely to experience BCR, or unlikely to experience BCR. The classification is based, at least in part, on the probability, the set of FOrge features, the patient specific SOI mask, or the image. In one embodiment, classifying the region of tissue as likely to experience BCR or unlikely to experience BCR may include classifying the region as likely to experience BCR when the machine learning classifier provides a probability of 0.5 or greater. In another embodiment, classifying the region of tissue as likely to experience BCR may be based on other probability values (e.g., 0.6, 0.7). In another embodiment, classifying the region of tissue may include categorizing the region of tissue based on more than two categories. For example, the region of tissue may be classified as one of "BCR+", "unknown", or "BCR−" based on the probability. Other categorization schemes may be employed. In another embodiment, method 500 generates a classification of the region of tissue as a progressor or non-progressor based, at least in part, on the second probability.

In another embodiment, method 500 further includes generating a cancer treatment plan. The cancer treatment plan is based, at least in part, on the classification, and at least one of the probability, the set of FOrge features, or the image. In one embodiment, the cancer treatment plan defines an immunotherapy agent dosage or schedule. In another embodiment, the cancer treatment plan defines a chemotherapy treatment agent or schedule, or defines a surgical procedure (e.g., biopsy, prostatectomy).

In one embodiment, method 500 further includes displaying the classification, the probability, the set of FOrge features, the patient-specific SOI mesh, the patient-specific SOI mask, the SOI mask, or the image. In another embodiment, method 500 further includes printing the cancer treatment plan, the classification, the probability, the set of FOrge features, or the image. In one embodiment, method 500 further includes controlling a personalized medicine system or CADx system to display the cancer treatment plan. In this embodiment, method 500 may include controlling the personalized medicine system or CADx system to display the cancer treatment plan, the classification, the probability, the set of FOrge features, the patient-specific SOI mesh, the patient-specific SOI mask, the SOI mask, or the image.

Figure 6:
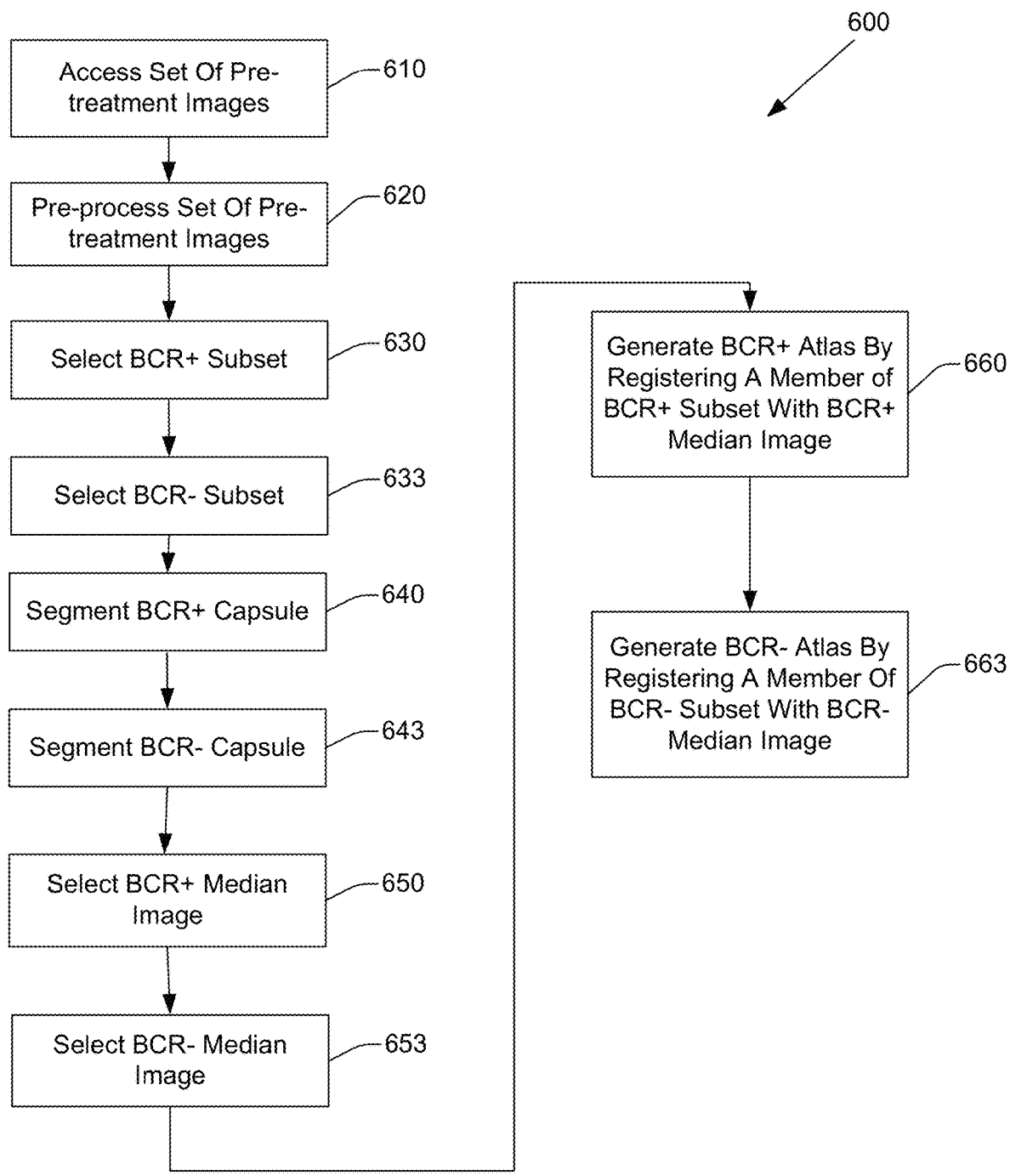
FIG. 6 illustrates an example method for generating a BcR atlas.

In one embodiment, method 500 further includes generating a BCR+ atlas, and a BCR− atlas. FIG. 6 illustrates an example method 600 for generating a BCR+ atlas and a BCR− atlas that is suitable for implementation by methods, apparatus, processors, and other embodiments described herein. Method 600 includes, at 610, accessing a set of pre-treatment images of a region of tissue demonstrating PCa. Accessing the set of pre-treatment images includes acquiring electronic data, reading from a computer file, receiving a computer file, reading from a computer memory, or other computerized activity. The set of pre-treatment images includes a plurality of BCR+ images, and a plurality of BCR− images. In one embodiment, a first region of tissue represented in a first member of the set of pre-treatment images has a Gleason score within a threshold of a second region of tissue represented in a second, different member of the set of pre-treatment images. In this embodiment, first region of tissue has a tumor stage within a threshold of the second region of tissue. Members of the set of pre-treatment images may be T1 W or T2 W MRI images. In another embodiment, members of the set of pre-treatment images may be acquired using other, different imaging modalities.

Method 600 also includes, at 620, generating a pre-processed set by pre-processing the set of pre-treatment images. In one embodiment, pre-processing the set of pre-treatment images includes using N4 bias field correction to reduce magnetic bias. In another embodiment, other pre-processing techniques may be employed.

Method 600 also includes, at 630, selecting a BCR+ subset from the pre-processed set. Method 600 also includes, at 633, selecting a BCR− subset from the pre-processed set. In one embodiment, the BCR+ subset and the BCR− subset are the same size. In another embodiment, the BCR+ subset and the BCR− subset are within a threshold of the same size.

Method 600 also includes, at 640, segmenting a prostate capsule represented in a member of the BCR+ subset. Method 600 also includes, at 643, segmenting a prostate capsule represented in a member of the BCR− subset. In one embodiment, a statistical shape and appearance model-based segmentation technique is employed.

Method 600 also includes, at 650, selecting a BCR+ median image from the BCR+ subset. Method 600 also includes, at 653, selecting a BCR− median image from the BCR− subset. Selecting a BCR+ median image or a BCR− median image includes selecting the BCR+ image or BCR− image that includes the prostate with the median volume for the respective subset.

Method 600 also includes, at 660, generating a BCR+ atlas by registering a member of the BCR+ subset to the BCR+ median image. Method 600 further includes, at 670, generating a BCR− atlas by registering a member of the BCR− subset to the BCR− median image.

Figure 7:
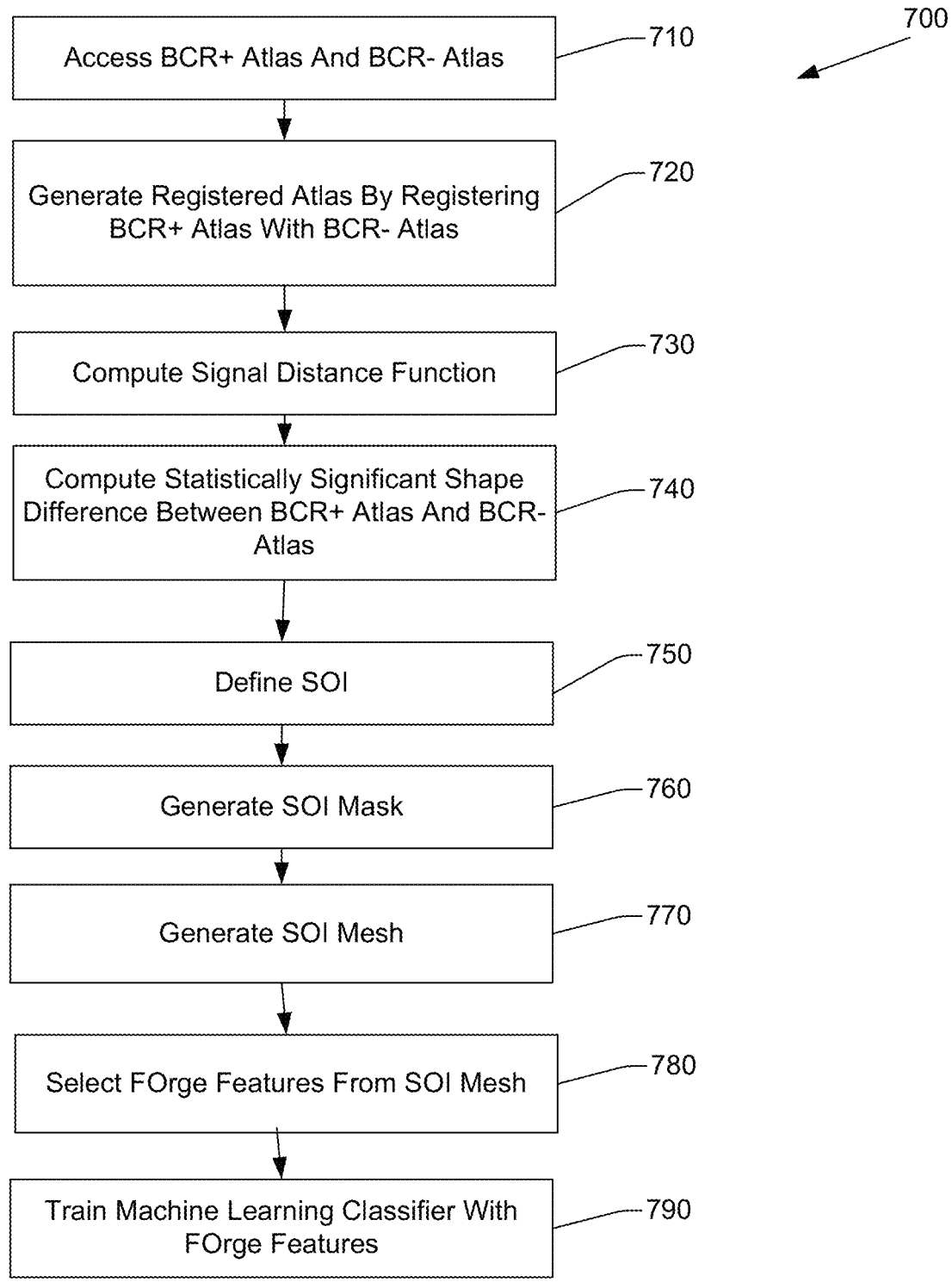
FIG. 7 illustrates an example method for training a machine learning classifier to predict BcR.

In one embodiment, method 500 or method 600 may further include training the machine learning classifier. FIG. 7 illustrates an example method 700 for training a machine learning classifier to predict BCR that is suitable for use by example methods, apparatus, processors, systems, and other embodiments described herein. Method 700 includes, at 710, accessing the BCR+ atlas and the BCR− atlas. Accessing the BCR+ atlas and the BCR− atlas includes acquiring electronic data, reading from a computer file, receiving a computer file, reading from a computer memory, or other computerized activity.

Method 700 also includes, at 720, generating a registered atlas by registering the BCR+ atlas with the BCR− atlas.

Method 700 also includes, at 730, computing a signal distance function from the registered atlas.

Method 700 also includes, at 740, computing statistically significant shape differences between the BCR+ atlas and the BCR− atlas. Method 700 computes the statistically significant shape differences based, at least in part, on the registered atlas and the signal distance function.

Method 700 also includes, at 750, defining an SOI based on the statistically significant shape differences.

Method 700 also includes, at 760, generating an SOI mask from the SOI.

Method 700 also includes, at 770, generating an SOI mesh from the SOI mask. The SOI mesh includes a plurality of vertices. FOrge features may be extracted from a vertex.

Method 700 also includes, at 780, selecting a set of FOrge features from the SOI mesh. In one embodiment, FOrge features are extracted from every vertex in the SOI mesh. In another embodiment, FOrge features are extracted from a threshold number of vertices. Extracting FOrge features from a threshold number of vertices less than all the vertices in the SOI mesh may improve the performance of a computer performing methods described herein by reducing the computational complexity relative to conventional approaches which may require extracting features from every vertex.

In one embodiment, the set of FOrge features is selected using a random forest (RF) Gini impurity index. Selecting the FOrge features using the RF Gini impurity index facilitates selecting the most discriminative features. In one embodiment, the set of FOrge features includes a curvature magnitude feature, an XY plane surface normal orientation feature, an XZ plane surface normal orientation feature, a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature. In another embodiment, other, different features may be selected based, at least in part, on the RF Gini impurity index, or other selection criterion.

Method 700 further includes, at 790, training the machine learning classifier with the set of FOrge features. In one embodiment, training the machine learning classifier with the set of FOrge features includes training the machine learning classifier using three-cross validation. Embodiments may train the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

Improved identification or classification of patients who will experience BCR may produce the technical effect of improving treatment efficacy by increasing the accuracy of and decreasing the time required to treat patients demonstrating BCR in PCa or other forms of cancerous pathology. Treatments and resources, including expensive immunotherapy agents, may be more accurately tailored to patients with a likelihood of benefiting from said treatments and resources, including responding to immunotherapy, so that more appropriate treatment protocols may be employed, and expensive resources are not wasted. Controlling a personalized medicine system, a CADx system, or a cancer BCR or progression prediction system based on improved identification or classification of patients who will experience BCR or progression further improves the operation of the system, since unnecessary operations will not be performed.

Using a more appropriately modulated treatment may lead to less aggressive therapeutics being required for a patient or may lead to avoiding or delaying a biopsy, a resection, or other invasive procedure. When patients experiencing PCa who will more likely experience BCR or progression are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to conventional approaches.

While FIGS. 5, 6, and 7 illustrate various actions occurring in serial, it is to be appreciated that various actions illustrated in FIG. 5 could occur substantially in parallel. By way of illustration, a first process could involve segmenting a prostate capsule represented in a pre-treatment MRI image, a second process could involve extracting FOrge features, and a third process could involve classifying a region of tissue represented in the pre-treatment MRI image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods described or claimed herein including method 500, 600, or 700. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 8:
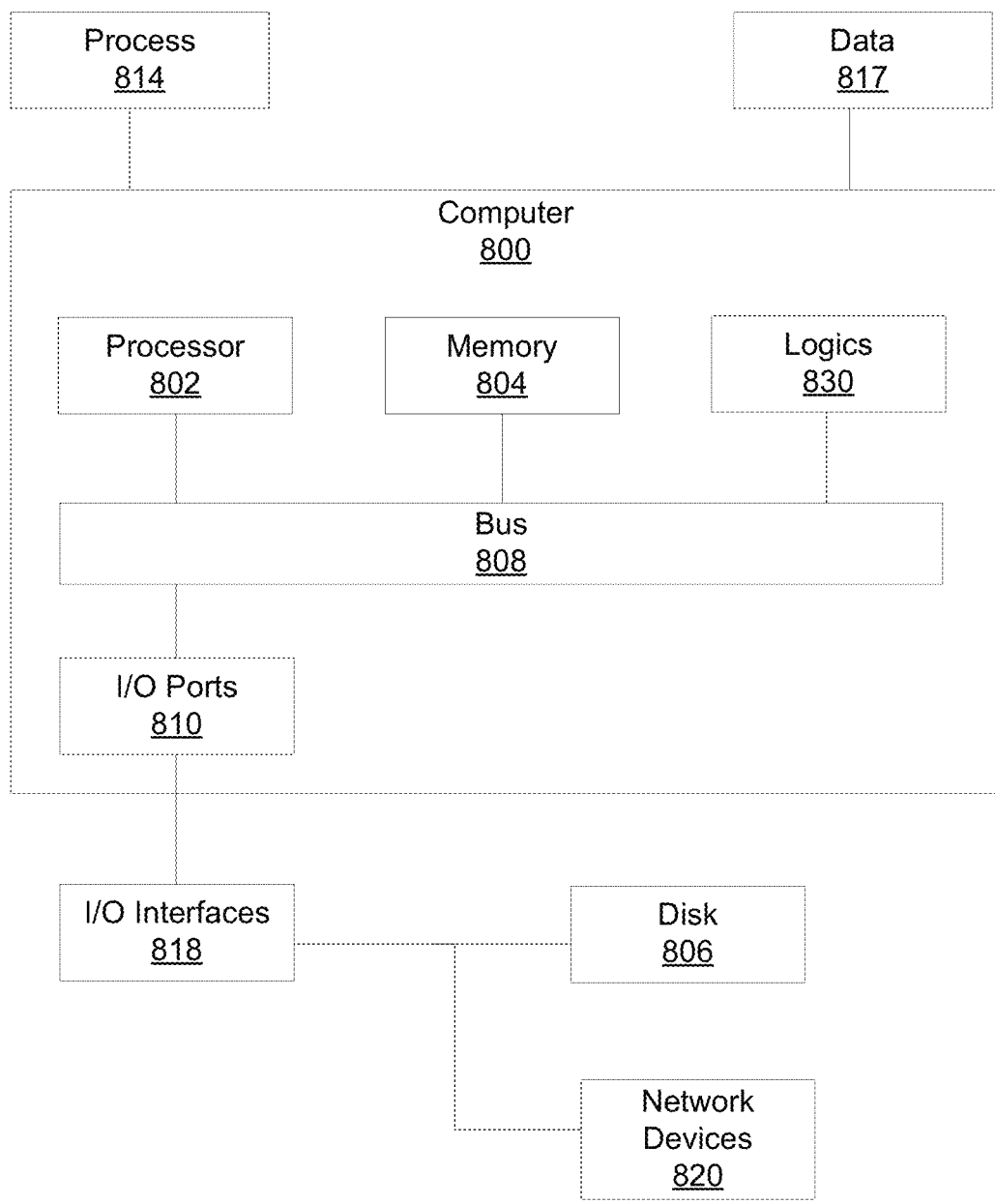
FIG. 8 illustrates an example computer in which example embodiments described herein may operate.

FIG. 8 illustrates an example computer 800 in which example methods illustrated herein can operate and in which example methods, apparatus, circuits, operations, or logics may be implemented. In different examples, computer 800 may be part of a personalized medicine system, a cancer progression or recurrence prediction system, a digital whole slide scanner, a CT system, may be operably connectable to a CT system, an MRI system, a personalized medicine system, or a digital whole slide scanner, or may be part of a CADx system.

Computer 800 includes a processor 802, a memory 804, and input/output (I/O) ports 810 operably connected by a bus 808. In one example, computer 800 may include a set of logics or circuits 830 that perform a method of predicting cancer progression or recurrence using a machine learning classifier. Thus, the set of circuits 830, whether implemented in computer 800 as hardware, firmware, software, and/or a combination thereof may provide means (e.g., hardware, firmware, circuits) for predicting cancer BCR based on FOrge features and a machine learning classifier. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized MRI images of a region of tissue demonstrating PCa. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting cancer recurrence, or cancer progression, according to embodiments and examples described.

One example embodiment includes a computer-readable storage device storing computer-executable instructions that, in response to execution, cause a BCR prediction system, a CADx system, a personalized medicine system, or a processor, to perform operations. The operations may include accessing an image of a region of tissue demonstrating cancerous pathology, where the image includes a plurality of voxels, a voxel having an intensity. The image may be a digitized three-dimensional (3D) pre-treatment MRI image of a region of tissue demonstrating PCa, where the image includes a segmented prostate capsule. In another embodiment, the image is a pre-treatment image of a region of tissue demonstrating another, different type of cancer.

A BCR prediction system, a personalized medicine system, or a processor may include circuitry such as, but not limited to, one or more single-core or multi-core processors. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The operations may also include registering the segmented prostate capsule to a biochemical recurrence negative (BCR−) median template. In one embodiment, registering the segmented prostate capsule with the BCR− median template includes registering the segmented prostate capsule with the BCR− median template using a rigid registration technique.

The operations may also include generating a registered SOI mask by registering a surface of interest (SOI) mask to the registered segmented prostate capsule. In one embodiment, registering the SOI mask with the registered segmented prostate includes registering the SOI mask with the registered segmented prostate using a B-spline registration technique.

The operations may also include generating a patient-specific SOI mask from the registered SOI mask.

The operations may also include generating a patient-specific SOI mesh from the patient-specific SOI mask. The patient-specific SOI mesh includes a plurality of vertices.

The operations may also include extracting a set of field effect induced organ distension (FOrge) features from the patient-specific mesh. FOrge features may be extracted from a vertex of the patient-specific SOI mesh. The set of FOrge features includes a curvature magnitude feature, an XY plane surface normal orientation feature, an XZ plane surface normal orientation feature, and a set of statistical features derived from the curvature magnitude feature, the XY plane surface normal orientation feature, and the XZ plane surface normal orientation feature.

The operations may also include computing a probability that the region of tissue will experience BCR based, at least in part, on the set of FOrge features. Computing the probability may include, in one embodiment, providing the FOrge features to a machine learning classifier. Providing the FOrge features to a machine learning classifier includes acquiring electronic data, reading from a computer file, receiving a computer file, reading from a computer memory, or other computerized activity. In one embodiment, the machine learning classifier is a random forest classifier. In this embodiment, the machine learning classifier computes a probability that the region of tissue will experience BCR based, at least in part on the FOrge features. In one embodiment, the operations further include training the machine learning classifier. In one embodiment, the operations further include testing the machine learning classifier on a held-out testing dataset. In another embodiment, the operations may include computing a second probability that the region of tissue will experience cancer progression based, at least in part on the FOrge features. In another embodiment, the machine learning classifier may be an SVM, a QDA classifier, an LDA classifier, a CNN, or other type of machine learning classifier.

The operations may also include classifying the region of tissue as likely to experience BCR or unlikely to experience BCR based, at least in part, on the probability. In one embodiment, the region of tissue is classified as likely to experience BCR when the probability has a value of 0.5 or greater. In another embodiment, the region of tissue is classified as likely to experience BCR when the probability has another, different value. In one embodiment, the region of tissue is classified with an AUC of at least 0.70. In another embodiment, the operations include generating a classification of the region of tissue as likely to experience cancer progression or unlikely to experience cancer recurrence based, at least in part, on the second probability.

The operations may further include displaying the classification, the probability, the set of FOrge features, the patient-specific SOI mesh, the patient-specific SOI mask, or the image. Displaying the classification, the probability, the set of FOrge features, the patient-specific SOI mesh, the patient-specific SOI mask, or the image may include displaying the classification, the probability, the set of FOrge features, the patient-specific SOI mesh, the patient-specific SOI mask, or the image, on a computer monitor, a smartphone display, a laptop computer display, a tablet computer display, or other display.

The operations may further include generating a cancer treatment plan based, at least in part, on the classification, and at least one of the probability, the set of FOrge features, or the image. In one embodiment, the cancer treatment plan may include an immunotherapy agent dosage or schedule, a chemotherapy agent dosage or schedule, or a surgical procedure plan.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting prostate cancer (PCa) biochemical recurrence (BCR), the apparatus comprising:
    a processor;
    a memory;
    an input/output (I/O) interface;
    a set of circuits including an image acquisition circuit, a segmentation circuit, a registration circuit, a mask circuit, a field effect induced organ distension (FOrge) circuit, and a classification circuit; and
    an interface that connects the processor, the memory, the I/O interface, and the set of circuits;
    where the memory is configured to store an image of a region of tissue demonstrating PCa, a BCR negative (BCR−) median template, and a surface of interest (SOI) mask, the image having a plurality of voxels, a voxel having an intensity;
    where the image acquisition circuit is configured to access a pre-treatment image of a region of tissue demonstrating PCa;
    where the segmentation circuit is configured to generate a segmented prostate by segmenting a prostate capsule represented in the pre-treatment image;
    where the registration circuit is configured to:
        generate a registered prostate by registering the segmented prostate with the BCR− median template; and
        generate a registered SOI mask by registering the SOI mask with the registered prostate;
    where the mask circuit is configured to:
        generate a patient-specific SOI mask from the registered prostate and the registered SOI mask; and
        generate a patient-specific SOI mesh from the patient-specific SOI mask;
    where the FOrge circuit is configured to:
        extract a set of FOrge features from the patient-specific SOI mesh; and
        compute a probability that the region of tissue will experience BCR based, at least in part, on the set of FOrge features; and
    where the classification circuit is configured to classify the region of tissue as likely to experience BCR or unlikely to experience BCR based, at least in part, on the probability.

2. The apparatus of claim 1, where the registration circuit is configured to register the segmented prostate with the BCR− median template using a rigid registration technique.

3. The apparatus of claim 1, where the registration circuit is configured to register the SOI mask with the registered prostate using a B-spline registration technique.

4. The apparatus of claim 1, where the set of FOrge features includes a curvature magnitude feature, an XY plane surface normal orientation feature, an XZ plane surface normal orientation feature, a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature.

5. The apparatus of claim 1, where the FOrge circuit includes a machine learning component configured to compute the probability based on the set of FOrge features.

6. The apparatus of claim 5, where the machine learning component is configured as a random forest (RF) classifier having a depth of two, and 10000 trees.

7. The apparatus of claim 5, the set of circuits further comprising a training circuit configured to train the machine learning component.

8. The apparatus of claim 1, the set of circuits further including a display circuit configured to display the classification, the probability, the patient-specific SOI mask, or the pre-treatment image.

9. A non-transitory computer-readable storage device storing computer-executable instructions that when executed by a computer control the computer to perform a method for predicting biochemical recurrence (BCR), the method comprising:
    accessing a pre-treatment image of a region of tissue demonstrating prostate cancer (PCa), where the image includes a plurality of voxels, a voxel having an intensity;
    segmenting a prostate capsule represented in the image;
    registering the segmented prostate with a BCR negative (BCR−) median template;
    registering a surface of interest (SOI) mask with the registered segmented prostate;
    generating a patient-specific SOI mask from the registered SOI;
    generating a patient-specific SOI mesh from the patient-specific SOI mask, where the SOI mesh includes a plurality of vertices;
    extracting a set of field effect induced organ distension (FOrge) features from the patient-specific SOI mesh;
    providing the set of FOrge features to a machine learning classifier;
    receiving, from the machine learning classifier, a probability that the region of tissue will experience BCR based on the set of FOrge features;
    classifying the region of tissue as likely to experience BCR, or unlikely to experience BCR based, at least in part, on the probability, the set of FOrge features, the patient specific SOI mask, or the image.

10. The non-transitory computer-readable storage device of claim 9, where the image is a three dimensional (3D) magnetic resonance imaging (MRI) image.

11. The non-transitory computer-readable storage device of claim 9, where segmenting the prostate capsule includes segmenting the prostate capsule using a statistical shape and appearance model segmentation technique.

12. The non-transitory computer-readable storage device of claim 9, where registering the segmented prostate with the BCR− median template includes registering the segmented prostate with the BCR− median template using a rigid registration technique.

13. The non-transitory computer-readable storage device of claim 9, where registering the SOI mask with the registered segmented prostate includes registering the SOI mask with the registered segmented prostate using a B-spline registration technique.

14. The non-transitory computer-readable storage device of claim 9, where the set of FOrge features includes a curvature magnitude feature, an XY plane surface normal orientation feature, and an XZ plane surface normal orientation feature.

15. The non-transitory computer-readable storage device of claim 14, where the set of FOrge features further includes a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature.

16. The non-transitory computer-readable storage device of claim 9, where the machine learning classifier is a random forest (RF) classifier.

17. The non-transitory computer-readable storage device of claim 16, where the RF classifier has a depth of two, and 10000 trees.

18. The non-transitory computer-readable storage device of claim 9, the method further comprising displaying the classification, the probability, the set of FOrge features, the patient-specific SOI mesh, the patient-specific SOI mask, the SOI mask, or the image.

19. The non-transitory computer-readable storage device of claim 9, the method further comprising generating a BCR positive (BCR+) atlas and a BCR− atlas.

20. The non-transitory computer-readable storage device of claim 19, where generating the BCR+ atlas and the BCR-atlas comprises:
  accessing a set of pre-treatment images of a region of tissue demonstrating PCa, where the set of pre-treatment images includes a plurality of BCR+ images, and a plurality of BCR− images;
  generating a pre-processed set by pre-processing the set of pre-treatment images using N4 bias field correction to reduce magnetic bias;
  selecting a BCR+ subset from the pre-processed set;
  selecting a BCR− subset from the pre-processed set;
  segmenting a prostate capsule represented in a member of the BCR+ subset;
  segmenting a prostate capsule represented in a member of the BCR− subset;
  selecting a BCR+ median image from the BCR+ subset;
  selecting a BCR− median image from the BCR− subset;
  generating a BCR+ atlas by registering a member of the BCR+ subset to the BCR+ median image;
  generating a BCR− atlas by registering a member of the BCR− subset to the BCR− median image.

21. The non-transitory computer-readable storage device of claim 20, where a first region of tissue represented in a first member of the set of pre-treatment images has a Gleason score within a threshold of a second region of tissue represented in a second, different member of the set of pre-treatment images, and where the first region of tissue has a tumor stage within a threshold of the second region of tissue.

22. The non-transitory computer-readable storage device of claim 20, where the BCR+ subset and the BCR− subset are the same size.

23. The non-transitory computer-readable storage device of claim 20, the method further comprising training the machine learning classifier.

24. The non-transitory computer-readable storage device of claim 23, where training the machine learning classifier comprises:
  accessing the BCR+ atlas and the BCR− atlas;
  generating a registered atlas by registering the BCR+ atlas with the BCR− atlas;
  computing a signal distance function from the registered atlas;
  computing statistically significant shape differences between the BCR+ atlas and the BCR− atlas based, at least in part, on the registered atlas;
  defining an SOI based on the statistically significant shape differences;
  generating an SOI mask from the SOI;
  generating an SOI mesh from the SOI mask;
  selecting a set of FOrge features from the SOI mesh; and
  training the machine learning classifier with the set of FOrge features using three-cross validation.

25. The non-transitory computer-readable storage device of claim 24, where the set of FOrge features is selected using a random forest (RF) Gini impurity index.

26. The non-transitory computer-readable storage device of claim 25, where the set of FOrge features includes a curvature magnitude feature, an XY plane surface normal orientation feature, an XZ plane surface normal orientation feature, a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature.

27. A non-transitory computer-readable storage device storing instructions that when executed by a processor control the processor to perform operations, the operations including:
  accessing a digitized three-dimensional (3D) pre-treatment image of a region of tissue demonstrating prostate cancer (PCa), where the image includes a segmented prostate capsule;
  generating a registered segmented prostate capsule by registering the segmented prostate capsule to a biochemical recurrence negative (BCR−) median template;
  generating a registered SOI mask by registering a surface of interest (SOI) mask to the registered segmented prostate capsule;
  generating a patient-specific SOI mask from the registered SOI mask;
  generating a patient-specific SOI mesh from the patient-specific SOI mask;
  extracting a set of field effect induced organ distension (FOrge) features from the patient-specific mesh, where the set of FOrge features includes a curvature magnitude feature, an XY plane surface normal orientation feature, an XZ plane surface normal orientation feature, and a set of statistical features derived from the curvature magnitude feature, the XY plane surface normal orientation feature, and the XZ plane surface normal orientation feature;

computing a probability that the region of tissue will experience BCR based, at least in part, on the set of FOrge features;

classifying the region of tissue as likely to experience BCR or unlikely to experience BCR based, at least in part, on the probability; and displaying the classification, the probability, the set of FOrge features, the patient-specific SOI mesh, the patient-specific SOI mask, or the image.

* * * * *